US010058296B2

(12) United States Patent
Yun et al.

(10) Patent No.: US 10,058,296 B2
(45) Date of Patent: Aug. 28, 2018

(54) COMPUTED TOMOGRAPHY SYSTEM HAVING COOLING SYSTEM

(71) Applicant: Samsung Electronics Co., Ltd., Gyeonggi-do (KR)

(72) Inventors: Alexander Yun, Gyeonggi-do (KR); Sung-ki Kim, Seoul (KR); Chang-yeon Won, Seoul (KR); Jeong-min Na, Seoul (KR); Il Seong, Gyeonggi-do (KR); Tae-sik Cho, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 288 days.

(21) Appl. No.: 14/985,751

(22) Filed: Dec. 31, 2015

(65) Prior Publication Data
US 2016/0235377 A1    Aug. 18, 2016

(30) Foreign Application Priority Data

Feb. 12, 2015    (KR) .................. 10-2015-0021775

(51) Int. Cl.
*A61B 6/03*    (2006.01)
*H05G 1/02*    (2006.01)
*A61B 6/00*    (2006.01)

(52) U.S. Cl.
CPC ........... *A61B 6/4488* (2013.01); *H05G 1/025* (2013.01); *A61B 6/035* (2013.01); *A61B 6/405* (2013.01);
(Continued)

(58) Field of Classification Search
CPC .. A61B 6/00; A61B 6/03; A61B 6/035; A61B 6/44; A61B 6/4447; A61B 6/4488;
(Continued)

(56) References Cited

U.S. PATENT DOCUMENTS 6,909,775 B2    6/2005 Ray et al.
7,410,295 B2    8/2008 Distler et al.
(Continued)

FOREIGN PATENT DOCUMENTS

JP    10-160847 A    6/1998
JP    2008-164548 A    7/2008
(Continued)

OTHER PUBLICATIONS

Korean Search Report, dated Nov. 8, 2016.
(Continued)

*Primary Examiner* — Anastasia Midkiff
(74) *Attorney, Agent, or Firm* — Cha & Reiter, LLC (57) ABSTRACT

Cooling systems of a CT system and methods of cooling the CT system are disclosed. The CT system includes a gantry and a table that moves an object into a bore of the gantry, wherein the gantry includes a cover having a front surface in which at least an inlet slot is formed and a rear surface in which exhaust holes are formed along with exhaust fans in the rear surface of the cover of the gantry. Fans for the in-take and exhaustion of air are not required to be formed on the front surface of the cover of the gantry. A hole through which external air is taken in through the inlet slot is moved in a rotor of the gantry.

18 Claims, 10 Drawing Sheets

(52) U.S. Cl.
CPC ..... *A61B 6/4291* (2013.01); *A61B 2560/0406* (2013.01); *G01N 2223/31* (2013.01); *G01N 2223/3103* (2013.01)

(58) Field of Classification Search
CPC ............ A61B 2560/00; A61B 2560/02; A61B 2560/04; A61B 2560/0406; H05G 1/00; H05G 1/02; H05G 1/025; G01N 2223/00; G01N 2223/31; G01N 2223/3103
See application file for complete search history.

(56) References Cited

U.S. PATENT DOCUMENTS

| | | |
|---|---|---|
| 2004/0114723 A1 | 6/2004 | Ray et al. |
| 2007/0053500 A1* | 3/2007 | Distler ................... A61B 6/035 378/199 |
| 2009/0232281 A1 | 9/2009 | Jimbo et al. |
| 2010/0177863 A1 | 7/2010 | Jimbo et al. |
| 2010/0266096 A1 | 10/2010 | Sharpless |
| 2011/0228910 A1 | 9/2011 | Gregerson et al. |
| 2013/0129104 A1* | 5/2013 | Joshi ....................... A61B 6/032 381/71.3 |
| 2014/0254746 A1* | 9/2014 | Kodaira ................... A61B 6/03 378/4 |
| 2014/0378817 A1 | 12/2014 | Gregerson et al. |

FOREIGN PATENT DOCUMENTS

| | | |
|---|---|---|
| KR | 20-1998-0050546 U | 10/1998 |
| KR | 2003-0006348 A | 1/2003 |
| KR | 10-2014-0029296 | 3/2014 |

OTHER PUBLICATIONS

Korean Notice of Allowance, dated Jan. 6, 2017.
Korean Notice of Non-Final Rejection dated Mar. 3, 2016.
PCT International Search Report dated Apr. 27, 2016.

* cited by examiner

COMPUTED TOMOGRAPHY SYSTEM HAVING COOLING SYSTEM

CLAIM OF PRIORITY

This application claims the benefit of priority from Korean Patent Application No. 10-2015-0021775, filed on Feb. 12, 2015, in the Korean Intellectual Property Office, the disclosure of which is incorporated by reference herein in its entirety.

BACKGROUND

1. Field of the Disclosure

The present disclosure relates to computed tomography (CT) systems, and more particularly, to cooling systems of a CT system and methods of cooling the CT system.

2. Description of the Related Art

With recent advances in medical technology, various methods of obtaining internal information of a living body have been developed. In particular, a tomography system is now widely used. Moreover, with regard to tomography systems, a computed tomography (CT) system is now in widespread use. The CT system is a device for obtaining an image such that, after irradiating an X-ray toward an object from various angles, the X-ray that passes through the object is measured, and afterwards, the degree of absorption of the X-ray with respect to a cross-section is restructured to generate the image. In a general X-ray image, a three-dimensional (3D) shape of the object is displayed on a two-dimensional (2D) film. However, the CT system can display a 3D shape of a selected cross-section. Accordingly, various points of diagnosis that may not be found from a general X-ray image can be accurately determined if a 3D shape of a selected cross-section is displayed. Due to advantages such as the CT system being able to non-destructively and safely inspect an object, the CT system is widely used not only in medical fields but also in industrial fields to find an internal shape or density of an object.

A gantry of the CT system may include various parts. X-ray generation parts and other various parts of the CT system individually included in the gantry also include a cooling system. Each part mounted in the CT system includes at least one fan in a box to cool gantry parts. The fans for respective parts and an exhaust fan of the gantry of the CT system may be sources of noise in the overall CT system, and thus, the durability of the CT system may be reduced.

SUMMARY

The present disclosure provides at least one cooling system apparatus and method of a computed tomography (CT) system, in which the cooling system has an inlet slot formed on a front surface and exhaust holes formed on a rear surface of a gantry. The present disclosure includes methods for cooling the CT system.

Additional aspects of the present disclosure will be set forth in part in the description which follows and, in part, and will be apparent to a person of ordinary skill in the art from the description, and/or may be learned by practice of the presented embodiments by the person of ordinary skill in the art.

According to an aspect of the present disclosure, a cooling system of a computed tomography (CT) system includes a gantry and a table that moves an object into a bore of the gantry, wherein the gantry includes a cover having a front surface in which an inlet slot is formed and a rear surface in which exhaust holes are formed and exhaust fans formed in the rear surface of the cover of the gantry.

The inlet slot may be formed to have a shape surrounding a bore region of the gantry.

The inlet slot may have a "slit-shape" and more than one inlet slot may be formed.

The inlet slot may be formed between the front surface and a lateral surface of the cover.

The exhaust holes may be formed on regions corresponding to the inlet slot.

The cooling system may further include a rotor inside the cover of the gantry, wherein the rotor includes holes for air movement in which air taken into the gantry from the inlet slot moves.

The rotor may include a plurality of parts, and the parts may include holes for air movement through which air taken into the gantry is moved.

The exhaust fans may be formed only in the rear surface of the cover of the gantry.

According to another aspect of the present disclosure, a method of cooling the cooling system of the CT system described above includes the taking of external air into the gantry through the inlet slot formed in the front surface of the cover of the gantry and exhausting the air that has passed inside the gantry to the outside of the gantry through the exhaust holes formed in the rear surface of the cover of the gantry.

The gantry may include parts having holes therein, wherein the external air taken in through the inlet slot is moved to the exhaust holes through the holes.

External air taken into the gantry through the inlet slot is exhausted to the outside of the gantry through the exhaust holes by the exhaust fans.

BRIEF DESCRIPTION OF THE DRAWINGS

The above and/or other aspects of the present disclosure will be better understood and more readily appreciated by a person of ordinary skill in the art from the following description of the exemplary embodiments, taken in conjunction with the accompanying drawings in which.

DETAILED DESCRIPTION

A cooling system of a computed tomography (CT) system will now be described in detail with reference to certain embodiments, examples of which are illustrated in the accompanying drawings. As artisan will understand and appreciate that the appended claims are not limited to the aspects of the disclosure shown in the drawings. In the drawings, like reference numerals refer to like elements throughout and elements having the same numeral may be formed of the same material. Also, in the drawings, sizes of elements may be exaggerated for convenience and clarity of explanation.

Figure 1:
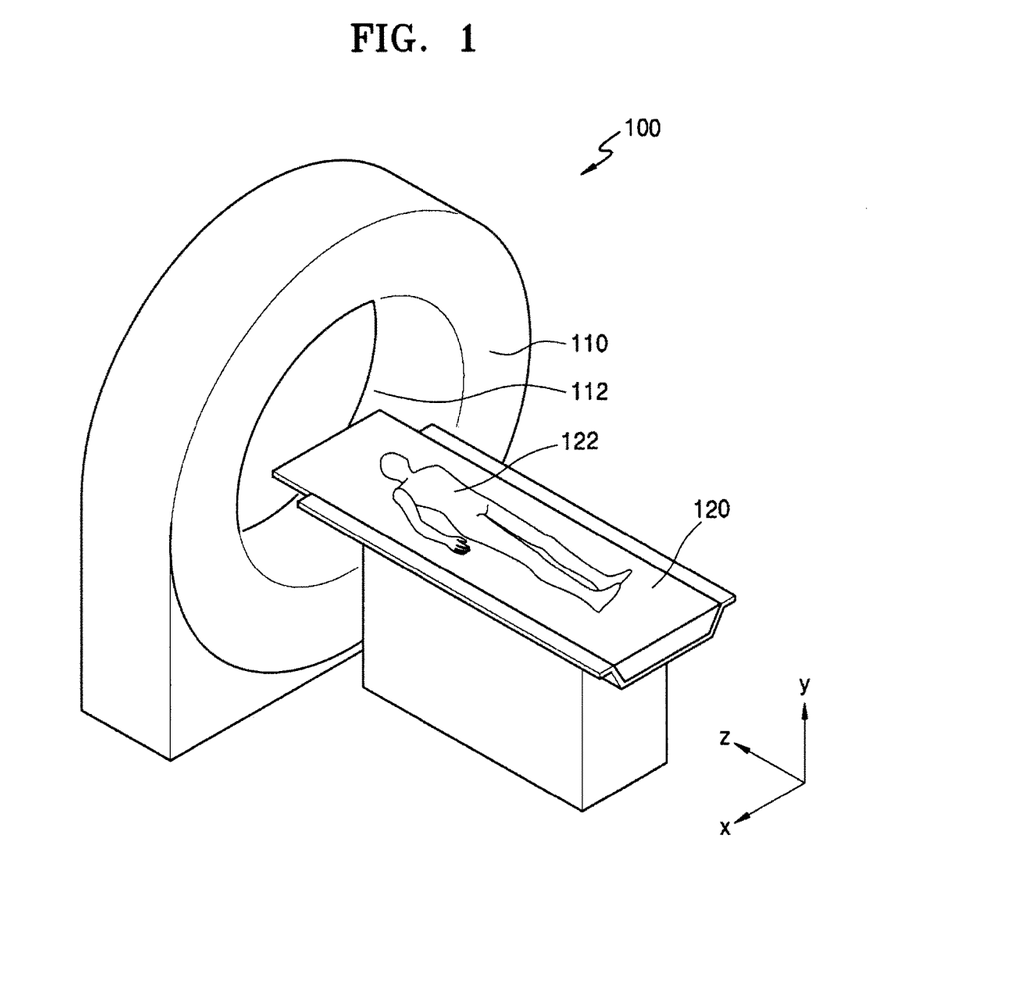
FIG. 1 is a perspective view of a cooling system for a computed tomography (CT) system according to an exemplary embodiment.

FIG. 1 is a schematic perspective view of a cooling system of a CT system 100 according to an embodiment of the disclosure.

Referring now to FIG. 1, the cooling system of the CT system 100 according to an exemplary embodiment includes a gantry 110 having a cylindrically shaped bore 112 in a center thereof and a table 120 that may transport an object 122 (such as a patient) into and out of the bore 112 of the gantry 110. The object 122 may be moved into the bore 112 of the gantry 110 by being positioned on the table 120. The table 120 may be moved in various directions, for example, in at least one of up, down, left, and right directions in the course of capturing a CT image, and also, may be tilted or rotated at a predetermined angle in a predetermined direction. Also, the gantry 110 may be tilted in a predetermined direction by a predetermined angle.

The object 122 may include a human or an animal, or part of a human or animal. For example, the object 122 may include organs such as a heart, liver, brain, breast, uterus, abdominal organ, spinal cord, or blood vessels. Also, the object 122 may include a phantom. The phantom may denote a material having a volume near to a density of a living thing and an actual effective atomic number, and may include a spherical phantom having a characteristic similar to a body.

The gantry 110 may include a stator unit that does not rotate and a rotor unit that includes various parts, such as an X-ray generator. Parts included in the gantry 110 may be an X-ray generator, an X-ray detector, a data acquisition system (DAS), a power supply, etc. just to name some non-limiting examples, and may be mounted in a cover or a housing of the gantry 110. When the CT system 100 is operated, the temperature inside the gantry 110 typically increases due to the operation of the parts in the gantry 110. In order to maintain the inner temperature of the gantry 110 at an appropriate level so as not to cause discomfort to a patient or possibly damage the electronic equipment, the gantry 110 of the cooling system of the CT system 100 according to an embodiment may include a cover having an inlet slot and an exhaust hole respectively formed in a front surface and a rear surface thereof. The cover that forms an external frame of the gantry 110 may be formed of plastic, etc.

Figure 2A:
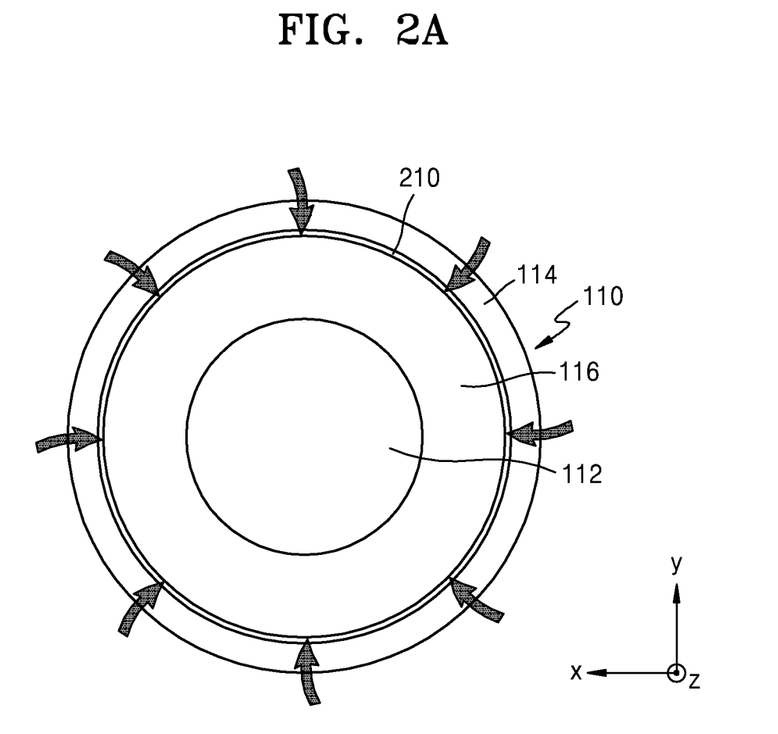
FIG. 2A is a front view of a gantry of a cooling system of a CT system with a circumferential inlet slot according to an aspect of the disclosure.
Figure 2B:
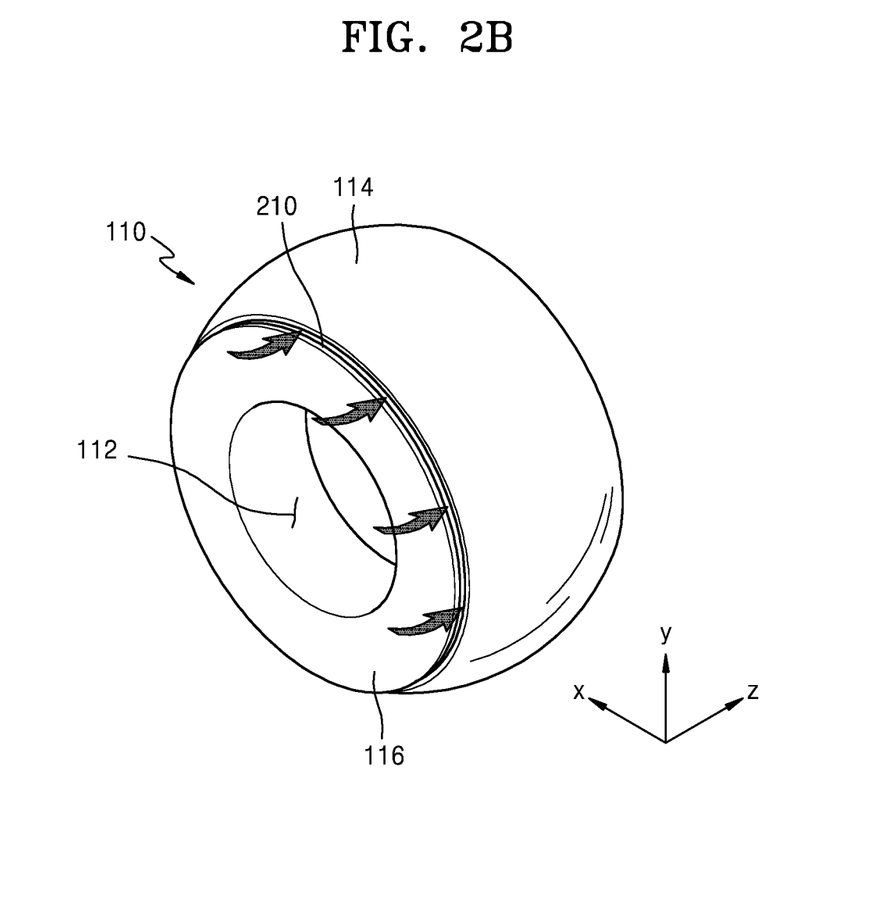
FIG. 2B is a perspective view of a gantry of a cooling system of a CT system according to an aspect of the disclosure.
Figure 2C:
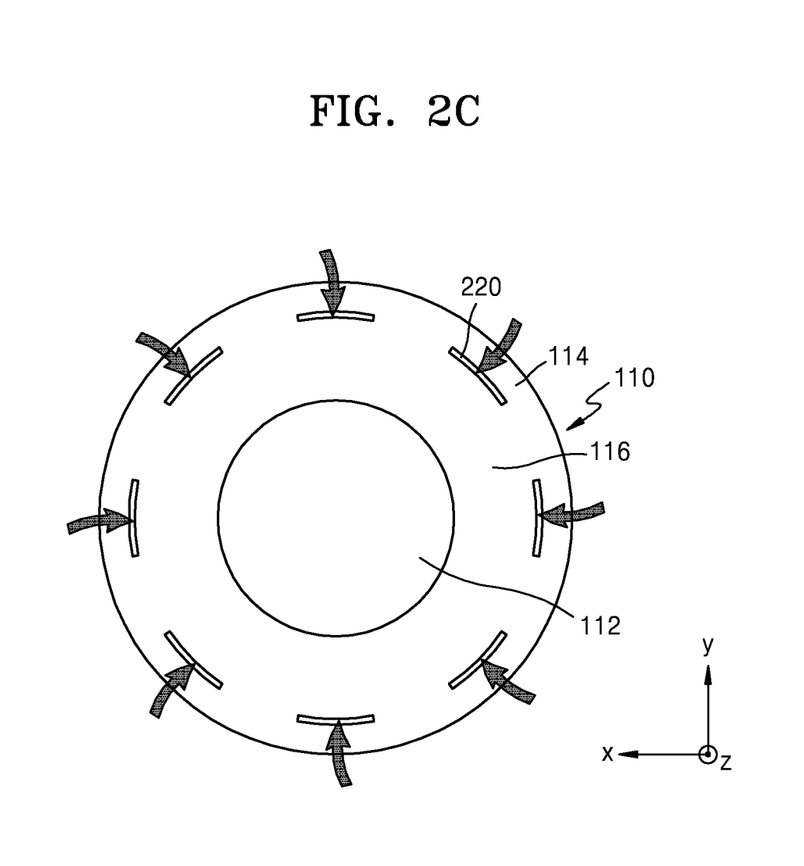
FIG. 2C is a front view showing a series of inlet slots of a gantry of a cooling system of a CT system according to another aspect of the disclosure.

FIGS. 2A and 2C are front views of the gantry 110 of the cooling system of the CT system 100 and FIG. 2B is a perspective view of the gantry 110 of the cooling system of the CT system 100 according to an embodiment. In particular, an inlet slot 210 may be formed on a front surface of the gantry 110.

Referring now to FIGS. 2A and 2B, the inlet slot 210 may be formed on a front surface 116 of the cover of the gantry 110. In the current exemplary embodiment, as depicted in FIG. 1, the front surface 116 of the gantry 110 may denote a region of the gantry 110 in a direction of the table 120 on which the object 122 is positioned. The cover that is an external surface of the gantry 110 may include a lateral unit 114 and a rear unit. The inlet slot 210 may be arranged in a region between the front surface 116 of the gantry 110 and the lateral unit 114. In this example, the inlet slot 210 may be formed as having a substantially circular shape that surrounds the bore 112 of the gantry 110. External air may be supplied into the gantry 110 through the inlet slot 210, and the air supplied from the outside may cool down various parts in the gantry 110. A width of the inlet slot 210 may be any size as long as air may pass through, for example, may be a few millimeters to a few tens of centimeters. The width of the inlet slot 210 may be formed so as to be constant according to regions, and may differ according to the regions. When external air having a lower temperature than that of air inside the gantry 110 enters into the gantry 110 through the inlet slot 210, the parts in the gantry 110 may be cooled down. Holes for facilitating air flow may be formed in a rotor ring which is a rotor unit in the gantry 110 and boxes of constituent parts.

Referring to FIG. 2C, a plurality of inlet slots 220 having a slit shape are formed on the front surface 116 of the cover of the gantry 110. In the current embodiment, the inlet slots 220 may be formed at specific intervals on a front surface of the gantry 110 and the shape thereof is not specifically limited. As depicted in FIGS. 2A and 2B, the inlet slot 210 may be formed as a circular shape surrounding the bore 112 of the gantry 110 or as depicted in FIG. 2C, the plurality of inlet slots 220 may be formed to have an overall circular shape. The shapes and numbers of the inlet slots 220 are not specifically limited to the examples shown and described. For example, the inlet slot 210 may be formed as a circular shape or a polygonal shape in a groove form.

Figure 3A:
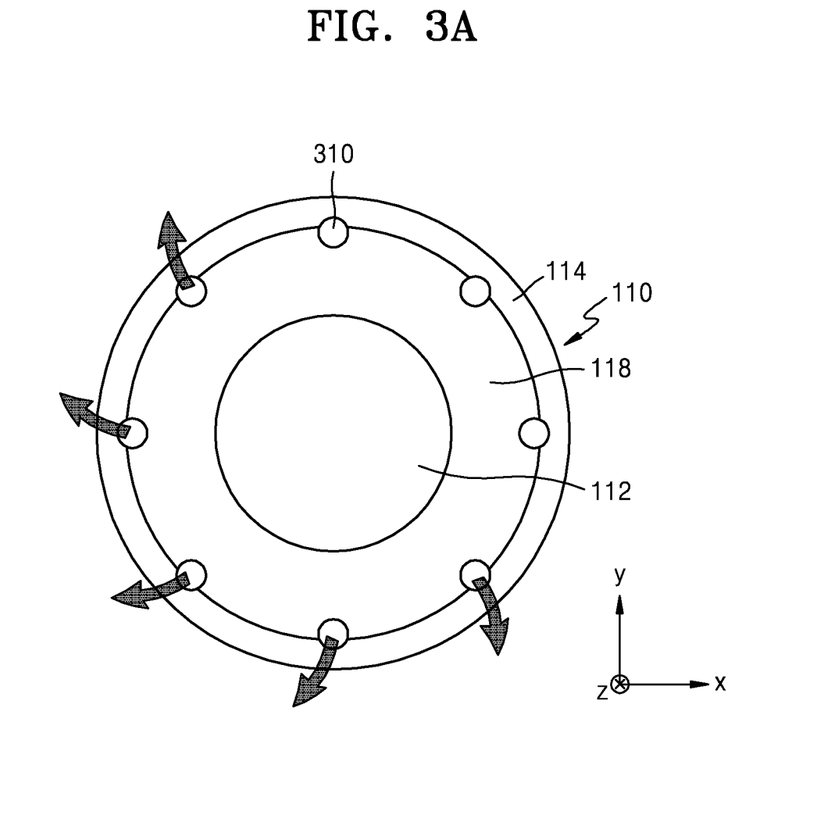
FIG. 3A is a rear view of a gantry of a cooling system of a CT system according to the present disclosure.
Figure 3B:
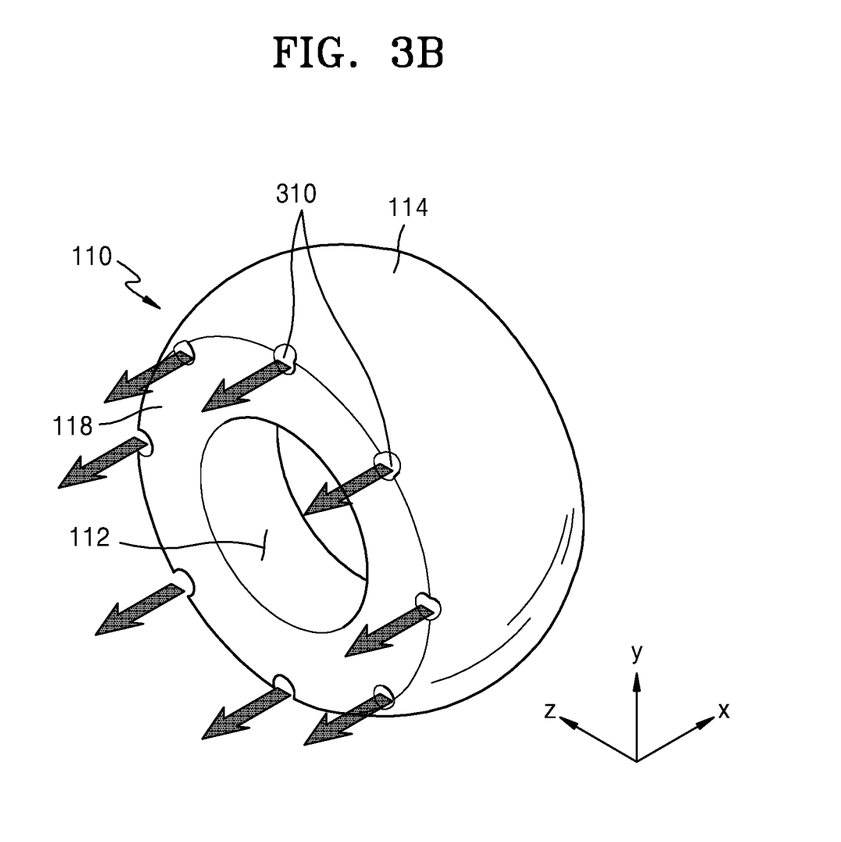
FIG. 3B is a perspective view of a gantry of a cooling system of a CT system according to the present disclosure and FIG. 3C is a rear view of a gantry of a cooling system of a CT system having exhaust fans according to the present disclosure.
Figure 3C:
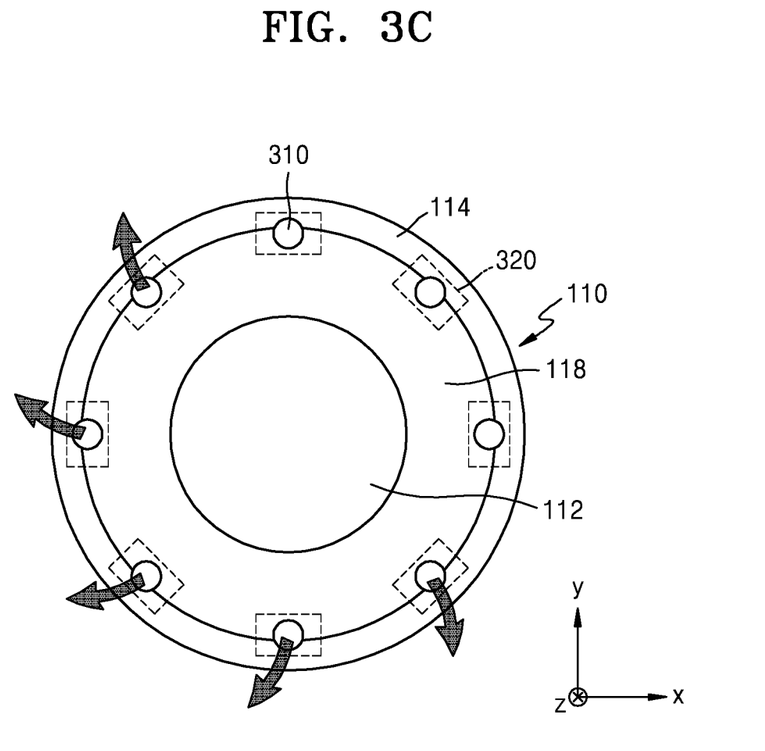

FIGS. 3A and 3C are rear views and FIG. 3B is a perspective view of the gantry 110 of the cooling system of the CT system 100 according to the present disclosure, and in particular, exhaust holes 310 formed on the rear surface of the gantry 110.

Referring now to FIGS. 3A and 3B, there are exhaust holes 310 that may be formed in a rear surface 118 of the cover of the gantry 110. Here, the rear surface 118 of the cover of the gantry 110 denotes a region behind the region of the gantry 110 facing the table 120 on which the object 122 shown in FIG. 1 is positioned. The exhaust holes 310 may be formed on regions between the rear surface 118 and a lateral surface 114 of the gantry 110. The exhaust holes 310 permit the exhaust of external air that has entered into the gantry 110 through the inlet slot 210 and the inlet slots 220 that are shown in FIGS. 2A through 2C.

In FIGS. 3A and 3B, the exhaust holes 310 have a circular shape. However, the shape of the exhaust holes 310 is not limited thereto, that is, as the inlet slot 210 depicted in FIG. 2A, the exhaust holes 310 may be formed as a circular shape surrounding the bore 112 of the gantry 110. Also, the exhaust holes 310 may be formed, for example, as having an oval shape, or having a polygonal cross-section, or a slit shape having a long side, just to name some non-limiting possibilities. The exhaust holes 310 have a width through which air may pass, and the size of the width is not specifically limited. For example, the width of the exhaust holes 310 may be in a range from about a few millimeters to about a few tens of centimeters. The width of the exhaust holes 310 may be formed uniform according to regions, and the width of the exhaust holes 310 may be changed according to portions.

Referring now to FIG. 3A, FIG. 3B and FIG. 3C, exhaust fans 320 (see FIG. 3C) may be arranged in the exhaust holes 310 formed on the rear surface 118 of the cover of the gantry 110. For example, the exhaust fans 320 may be formed to correspond to the exhaust holes 310 to assist in the communication of air via the exhaust holes 310, and may induce air in the gantry 110 to be exhausted to the outside through the exhaust holes 310. The exhaust fans 320 may be formed only in the exhaust holes 310 of the rear surface 118 of the cover of the gantry 110, and additional fans in some embodiments may not be formed on the front surface 116 of the cover of the gantry 110.

In the cooling system of the CT system 100 according to the current embodiment, in the exhaust holes 310 arranged in the rear surface 118 of the cover of the gantry 110, the exhaust fans 320 may be formed, but additional fans may not be present. Parts to be formed in the gantry 110 may include an X-ray generator, an X-ray detector, a data acquisition system (DAS), and a power supply. However, a fan for intake or exhaust air may not be formed on each of the parts.

Figure 4A:
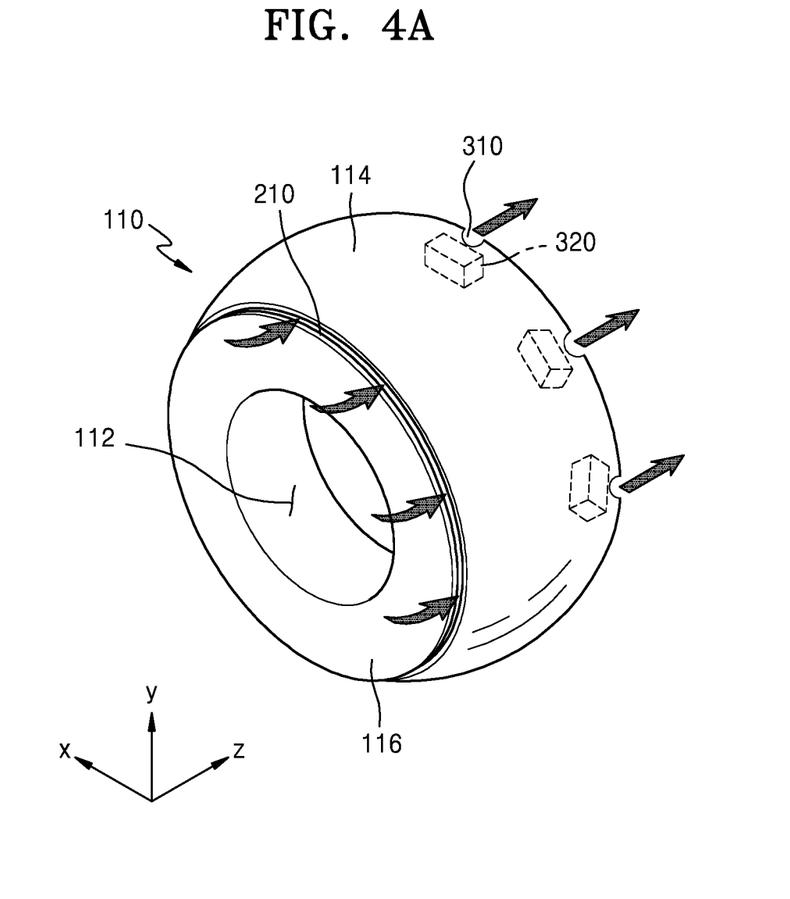
FIG. 4A is a perspective view and FIG. 4B is a side view illustrating a cooling method of a gantry of a cooling system of a CT system according to the present disclosure.
Figure 4B:
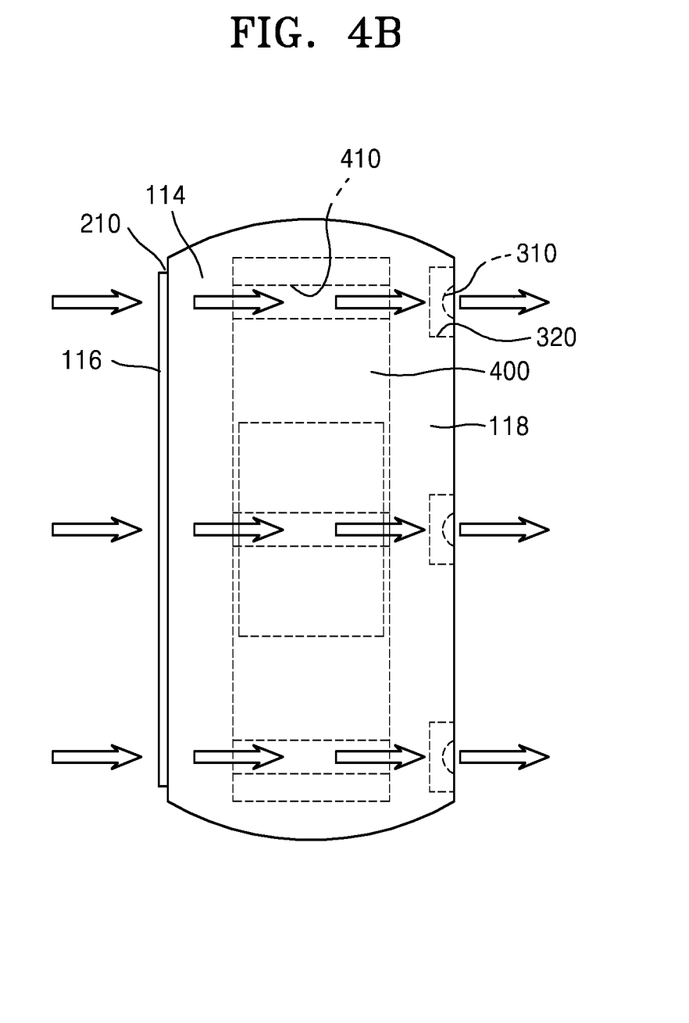

FIGS. 4A and 4B are respectively a perspective view and a lateral view illustrating a cooling method of the gantry 110 of the cooling system of the CT system 100 according to an embodiment.

Referring now to FIGS. 4A and 4B, external air may enter into the gantry 110 through the inlet slot 210 of the front surface 116 of the cover of the gantry 110, and the air that has passed through the inside of the gantry 110 may be exhausted to the outside through the exhaust holes 310 of the rear surface 118 of the cover of the gantry 110. The exhaust holes 310 may be formed parallel (to each other) in a z-direction to correspond to the inlet slot 210. The rotor 400, which is a rotation unit, and parts mounted on the rotor 400 may include holes 410 that provides a passageway through which the external air entered through the inlet slot 210 may move to the exhaust holes 310. After cooling the part mounted on the rotor 400 in the gantry 110, the flow of the external air may be induced by the exhaust fans 320. The flow of external air that is entered into the gantry 110 through the inlet slot 210 and is exhausted to the outside through the exhaust holes 310 in essentially a straight path, and thus may be expressed as a straight line in the z-direction. Thus, the method of cooling the CT system 100 according to the current embodiment may be referred to as a straight cooling system.

In the cooling system of the CT system 100 according to the current embodiment, the exhaust fans 320 may be formed on the rear surface 118 of the cover of the gantry 110, and intake fans or exhaust fans may not be formed on regions other than the rear surface 118 of the cover of the gantry 110. Also, an individual fan may not be included in each of the parts included in the gantry 110, for example, an X-ray generator, an X-ray detection unit, a DAS, and a power supply. Accordingly, through the whole CT system 100, in this embodiment, the exhaust fans 320 are formed only on the rear surface 118 of the cover of the gantry 110, and thus, an internal space of the gantry 110 may be more efficiently managed. Also, since the exhaust fans 320 are mounted on the rear surface 118 of the cover of the gantry 110, an additional fan may not be formed on the rotor 400 which is a rotation unit. Accordingly, when the cooling system of the CT system 100 according to the current embodiment is operated, a fan that has a rotating movement may not be situated in the gantry 110, and thus, a noise problem and duration may be improved. Also, since the exhaust fans 320 are located on the rear surface 118 of the cover of the gantry 110, when the fans are inspected or replaced, a maintenance job may be performed only with respect to the rear surface 118 of the cover of the gantry 110, and thus, maintenance management of the CT system 100 is easier.

Figure 5:
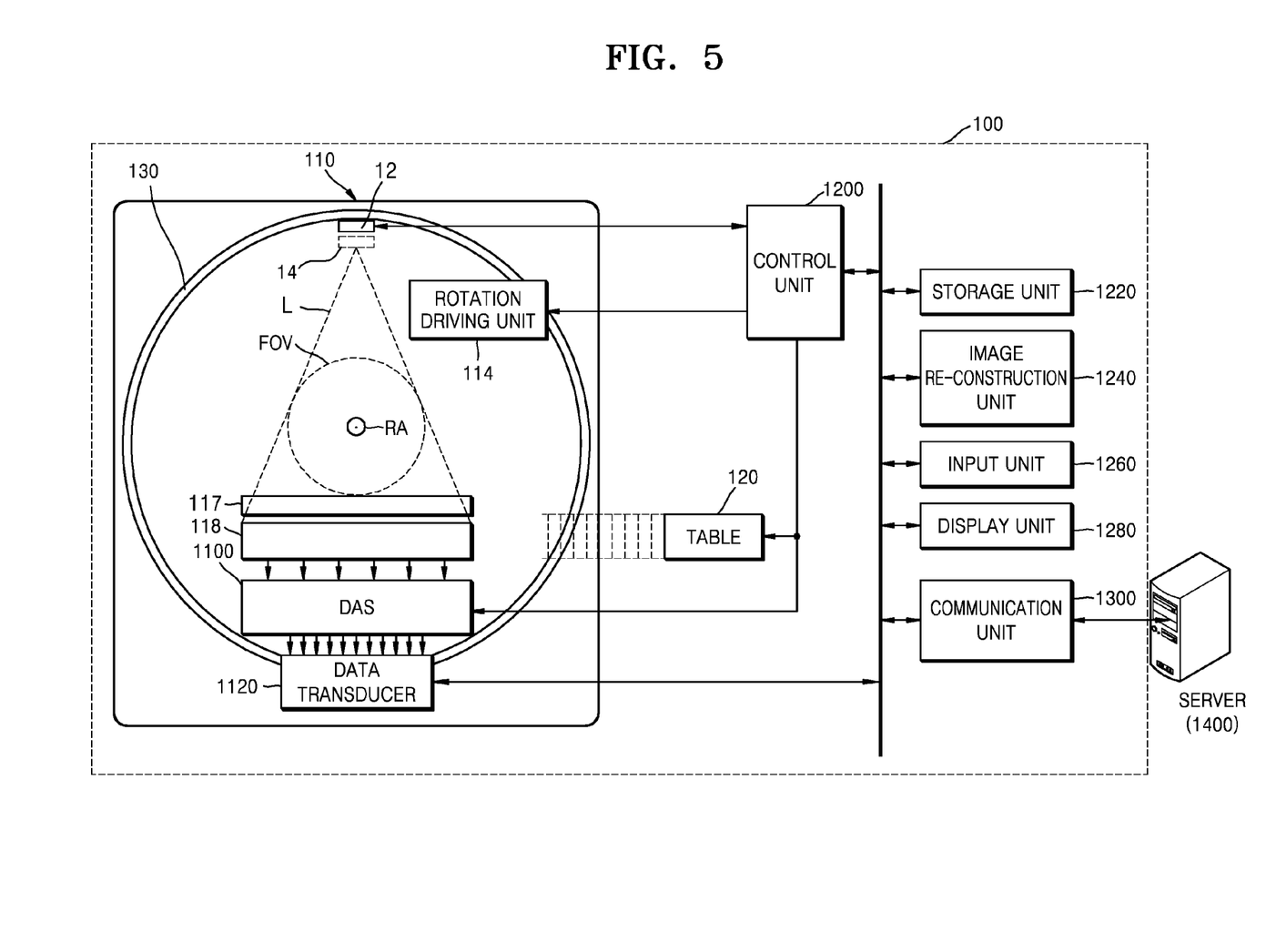
FIG. 5 is a schematic showing an overall configuration of a cooling system of a CT system according to the present disclosure.

FIG. 5 is a drawing showing an overall configuration of the cooling system of the CT system 100 according to another embodiment.

Referring to FIGS. 1 and 5, the cooling system of the CT system 100 according to an embodiment may include a gantry 110, a table 120, a control unit 1200 including hardware such as a processor, microprocessor with circuitry configured for operation, a non-transitory storage unit 1220 such as a memory, an image re-construction unit 1240, an input unit 1260, a display unit 1280 including hardware such as a display screen, and a communication unit 1300 including hardware such as a transmitter, receiver or transceiver. As described above, the object 122 may be positioned on the table 120, and the table 120 may move in predetermined directions, for example, up, down, left, and right directions by being controlled by the control unit 1200. The gantry 110 may include an X-ray generator 12, a collimator 14, an X-ray detector 118, a rotation driving unit 114 including hardware to rotate the rotation frame 130, a DAS 1100, and a data transducer 1120. The gantry 110 may include an annular type rotation frame 130 that is rotatable with respect to a predetermined rotation axis (RA). Also, the rotation frame 130 may be a disc type construction. The rotation frame 130 may include the X-ray generator 12 and the X-ray detector 118 that are respectively facing each other to have a predetermined field of view (FOV). Also, the rotation frame 130 may include an anti-scatter grid 117. The anti-scatter grid 117 may be located between the X-ray generator 12 and the X-ray detector 118.

In a medical imaging system, both an attenuated primary radiation that forms a useful image and also scattered radiation that reduces the quality of image may be included in an X-ray that reaches the X-ray detector 118 (or photosensitive film). In order to transmit majority of the primary radiation and to attenuate the scattered radiation, the anti-scatter grid 16 may be located between the object 122 and the X-ray detector 118. The anti-scatter grid 117 may be formed of a type in which interspace materials, such as, strips of a lead foil and a solid polymer material without a hollow or a solid polymer and a fiber composite material without a hollow, are alternately stacked. However, the configuration of the anti-scatter grid 117 is not necessarily limited thereto.

The rotation frame 130 may receive a driving signal from the rotation driving unit 114 and may rotate the X-ray generator 12 and the X-ray detector 118 at a predetermined speed. The rotation frame 130 may receive a driving signal and power from the rotation driving unit 114 in a contact method through, for example, a slip ring. Also, the rotation frame 130 may receive a driving signal and power from the rotation driving unit 114 via wireless communication.

The X-ray generator 12 may generate and emit an X-ray by receiving a voltage and a current, for example, from a power distribution unit (PDU) through a high voltage generation unit via a slip ring. When the high voltage generation unit applies a predetermined voltage, the X-ray generator 12 may generate X-rays having a plurality of energy spectrums corresponding to the predetermined voltage. The X-rays generated from the X-ray generator 12 may be emitted as a predetermined state by the collimator 14.

The object 122 may be moved into the bore 112 of the gantry 110 by being positioned on the table 120. An X-ray "L" generated from the X-ray generator unit 12 may be irradiated onto the object 122 through the collimator 14, and the X-ray L that passes through the object 122 may be detected by the X-ray detector 118, and thus, state information of the object may be obtained. The X-ray generator 12 may be configured to include various X-ray generation structures, and may include a plurality of electron emission sources. For example, the X-ray generator 12 may include electron emission sources that may emit electrons and an electrode unit that may emit X-rays due to the collision between emitted electrons and is formed of a conductive material. The electron emission sources may be formed of a material that may emit electrons, for example, a metal, silicon, an oxide, diamond, diamond like carbon (DLC), a carbon compound, a nitrogen compound, carbon nanotube, etc. The X-ray generation unit 12 may be formed by including a plurality of electron emission sources formed as a ring type. The X-ray generator 12 may change its location during an operation of the gantry 110 but may be fixedly disposed not to be rotated. Also, the X-ray generator 12 may be configured so that an electron gun may irradiate an X-ray in a direction towards the bore 112 of the gantry 110. However, the configuration of the X-ray generator 12 is not limited thereto, that is, may be any configuration as long as the X-ray generator 12 may emit an X-ray.

The X-ray detector unit 118 may include one or a plurality of X-ray detectors to detect an X-ray that is radiated from the X-ray generator 12 and is passed through the object 122 through the collimator 14, and the X-ray detectors may form an array structure. The X-ray detectors may form a single channel, but is not limited thereto. The X-ray detector unit 118 may include a multi-layer structure including a semiconductor layer and an electrode. The X-ray detection unit 118 may be formed as a ring shape as the same shape as the X-ray generator unit 12 on a lateral of the X-ray generation unit 12. The X-ray detection unit 118 may change its location during an operation of the gantry 110 but may be fixedly disposed not to be rotated. Also, the X-ray detector 118 may detect an X-ray that is generated from the X-ray generator 12 and is transmitted through the object 122 and may generate an electrical signal corresponding to the intensity of the detected X-ray.

The X-ray detector 118 may be connected to the DAS 1100. An electrical signal generated from the X-ray detector 118 may be collected by the DAS 1100. The electrical signal generated by the X-ray detection unit 118 may be collected at the DAS 1100 either with or without wire. Also, the electrical signal generated by the X-ray detection unit 118 may be provided to, for example, an analogue/digital converter through an amplifier. Only some of data collected from the X-ray detector 118 may be provided to the image re-construction unit 1240 according to slice thicknesses or number of slices, or some of the data may be selected by the image re-construction unit 1240. The digital signal may be provided to the image re-construction unit 1240 through the data transducer 1120. The digital signal may be transmitted to the image re-construction unit 1240 through the data transducer 1120 using wire or wirelessly.

The control unit 1200, which includes hardware such as a microprocessor or processor circuitry configured for operation, may control an operation of each module of the cooling system of the CT system 100. For example, the control unit 1200 may control operations of the table 120, the collimator 14, the rotation driving unit 114, the DAS 1100, the storage unit 1220, the image re-construction unit 1240, the input unit 1260, the display unit 1280, and the communication unit 1300. The image re-construction unit 1240 may receive data (for example, pure data before processing) obtained by the DAS 1100 through the data transducer 1120, and may perform a pre-processing process. The pre-processing may include a process of correcting non-uniform sensitivity between channels and a process of correcting signal loss due to rapid reduction of signal intensity or an X-ray absorbent, such as, a metal. An output data of the image re-construction unit 1240 may be referred to as a raw data or a projection data. The projection data may be stored in the storage unit 1220 together with image capturing conditions (for example, a tube voltage, an image capturing angle, etc.) when the image is captured. The projection data may be a set of data values corresponding to the intensities of X-rays that have passed through the object 122. The storage unit 1220 may include a non-transitory storage medium including at least one of a flash memory type, a hard disk type, a multimedia card micro type, a card type memory (SD, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disc, and an optical disc.

Also, the image re-construction unit 1240 may reconstruct cross-sectional images of the object 122 by using an obtained projection data set. The cross-sectional image may be 3 dimensional (3D) images. In other words, the image re-construction unit 1240 may generate a 3D image of the object 122 by using a cone beam reconstruction method based on the obtained projection data set. An external input with respect to X-ray tomography conditions, image processing conditions, etc. may be received through the input unit 1260. For example, the X-ray tomography conditions may include a plurality of tube voltages, the setting of energy values of a plurality of X-rays, the selection of shooting protocols, the selection of method of image reconstruction, the setting of a FOV region, the number of slices, slice thicknesses, and the setting of parameters for image post-processing, etc. Also, the image processing condition may include the resolution of image, the setting of attenuation coefficient with respect to an image, and the setting of combination ratio of the image, etc. The input unit 1260 may include a device for receiving an application of a predetermined pressure from the outside. For example, the input unit 1260 includes hardware and may include a microphone, a keyboard, a mouse, a joystick, a touch pad, a touch pen, a voice, and a gesture recognition device, etc. The display unit 1280 comprises a display screen that displays an image restructured by the control image re-construction unit 1240. Transmission and reception of data or power between the elements described above may be performed by using at least one of wires, wireless, and optical communication. The communication unit 1300 may perform communications with an external device or an external medical device through a server 1400.

In the cooling system of a CT system according to an embodiment, external air that is taken in through an inlet slot formed on a front surface of the cover of the gantry and the air inside the gantry is exhausted to the outside through the exhaust holes formed on a rear surface of the cover of the gantry, and thus, an efficient cooling system is provided.

In the cooling system of a CT system according to an embodiment, exhaust fans are additionally formed preferably on a rear surface of the cover of the gantry, and thus, an inside of the gantry is efficiently managed. Additional fans are not formed in a rotor of the gantry, and thus, a noise problem and durability of the CT system are improved.

While a cooling system of a CT system according to an embodiment has been described with reference to the accompanying figures. However, it will be understood by those of ordinary skill in the art that the embodiments should be considered in descriptive sense only and not for purposes of limitation. Also, it should be understood, however, that there is no intent to limit the appended claims to particular forms of the embodiments disclosed, but on the contrary, embodiments are to cover all modifications, equivalents, and alternatives falling within the scope of the disclosure.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor" "controller", or "control unit" constitute hardware in the claimed disclosure that contain circuitry that is configured for operation. In FIG. 5, the rotation driving unit 114, x-ray detection unit 118, storage unit 1220, image reconstruction unit 1240, input unit 1260, display unit 1280 and communication unit 1300 all include hardware. Under the broadest reasonable interpretation, the appended claims constitute statutory subject matter in compliance with 35 U.S.C. § 101 and none of the elements are software per se. No claim element herein is to be construed under the provisions of 35 U.S.C. 112, sixth paragraph, unless the element is expressly recited using the phrase "means for".

The definition of the terms "unit" or "module" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. § 101 and do not constitute software per se. For example, the image processor in the present disclosure, and any references to an input unit and/or an output unit both comprise hardware circuitry configured for operation.

What is claimed is:

1. A cooling system of a computed tomography (CT) system, comprising:
   a gantry having a bore region therein, wherein the gantry surrounds a rotation axis; and
   a table that moves into and out of the bore region of the gantry,
   wherein the gantry comprises:
   a cover having a front surface along which an inlet slot is formed and a rear surface having exhaust holes formed thereon,
   exhaust fans being formed in the rear surface of the cover of the gantry that communicate with the exhaust holes, and
   wherein the inlet slot, exhaust fans, and exhaust holes are configured to channel air parallel to an extension direction of the rotation axis through the gantry bore.

2. The cooling system of claim 1, wherein the inlet slot surrounds the bore region of the gantry.

3. The cooling system of claim 1, wherein the inlet slot has a slit-shape and more than one inlet slot is formed along the front surface.

4. The cooling system of claim 1, wherein the inlet slot is formed between the front surface and a lateral surface of the cover.

5. The cooling system of claim 1, wherein the exhaust holes are formed on regions corresponding to the inlet slot.

6. The cooling system of claim 1, further comprising a rotor inside the cover of the gantry, wherein the rotor comprises holes through which an intake of air from the inlet slot into the gantry moves, and wherein the holes form tunnels parallel to the extension direction of the rotation axis through the gantry bore.

7. The cooling system of claim 6, wherein the rotor comprises a plurality of parts, having holes through which the intake of air into the gantry moves.

8. The cooling system of claim 7, wherein the parts comprise at least one of an X-ray generator, an X-ray detector, a data acquisition system (DAS), and a power supply.

9. The cooling system of claim 1, wherein the exhaust fans are formed exclusively facing the rear surface of the cover of the gantry.

10. A method of cooling the cooling system of the CT system of claim 1, the method comprising:
    taking external air into the gantry through the inlet slot formed in a front surface of a cover of the gantry; and
    exhausting the air that has passed inside the gantry to the outside of the gantry through the exhaust holes formed in the rear surface of the cover of the gantry.

11. The method of claim 10, wherein the gantry comprises parts having holes formed therein, and wherein the external air taken in through the inlet slot moves to the exhaust holes through the holes.

12. The method of claim 10, wherein the inlet slot is configured to receive ambient temperature air into the gantry, causing the air to become exhaust, and wherein the exhaust fans cause the exhaust to exit to the outside of the gantry through the exhaust holes.

13. The method of claim 10, further comprising forming the inlet slot between the front surface and a lateral surface of the cover.

14. The method of claim 10, further comprising forming the exhaust holes on regions of the cover corresponding to the inlet slot.

15. The method of claim 10, further comprising providing a rotor inside the cover of the gantry, wherein the rotor has holes therein through which an intake of air from the inlet slot into the gantry moves.

16. The method of claim 10, further comprising providing a rotor inside the cover of the gantry, wherein the rotor includes a plurality of parts having holes through which an intake of air into the gantry moves.

17. The method of claim 16, wherein the plurality of parts comprise at least one of an X-ray generator, an X-ray detector, a data acquisition system (DAS), and a power supply.

18. The method of claim 10, wherein the exhaust fans are formed exclusively in the rear surface of the cover of the gantry.

\* \* \* \* \*